United States Patent [19]
Sigler et al.

[11] Patent Number: 5,525,474
[45] Date of Patent: Jun. 11, 1996

[54] PIPERIDINE ANALOGS AND CONJUGATES OF PROCAINAMIDE AND NAPA

[75] Inventors: Gerald F. Sigler; Charles F. Walter, both of Carmel, Ind.; Todd Glancy, Fairmount, Ind.; Erasmus Huber, Finning, Germany; Frank E. Klein, Eklton, Md.

[73] Assignee: Boehringer Mannheim Corporation, Indianapolis, Ind.

[21] Appl. No.: 190,348

[22] Filed: Jan. 31, 1994

[51] Int. Cl.$^6$ .......... G01N 33/542; C12N 9/96; C07D 207/273; C07D 211/60

[52] U.S. Cl. .......... 435/7.7; 435/7.93; 435/188; 436/545; 436/546; 436/815; 530/322; 530/388.9; 530/389.8; 530/404; 530/405; 546/208; 546/227

[58] Field of Search .......... 530/404, 388.9, 530/389.8, 405, 322; 435/7.7, 7.93, 188; 546/208, 227; 536/1.11, 18.7; 436/545, 546, 815

[56] References Cited

U.S. PATENT DOCUMENTS

| | | | |
|---|---|---|---|
| 4,235,969 | 11/1980 | Singh et al. | 435/188 |
| 4,673,763 | 6/1987 | Buckler et al. | 564/155 |

FOREIGN PATENT DOCUMENTS 199042  10/1986  European Pat. Off.

OTHER PUBLICATIONS

M. Brinkley, Bioconjugate Chem., vol. 3, pp. 2–3 (1992).
P. Mojaverian et al., J. Pharm. Sci., vol. 69, pp. 721–724 (1980).
A. Russell et al., Clin. Exp. Immunol., vol. 3, pp. 901–909 (1968).
L. Adams et al., Int. J. Immunopharmacol., vol. 15, No. 8, pp. 887–897 (1993).

*Primary Examiner*—Mary E. Ceperley
*Attorney, Agent, or Firm*—Marilyn L. Amick; Max J. Kenemore; D. Michael Young

[57] ABSTRACT

Novel derivatives of procainamide and N-acetylprocainamide (NAPA) are disclosed having the following formula:

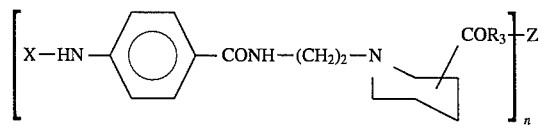

wherein:
X=hydrogen or acetyl;
n=1 to p where p=MW of Z/1000;
Z=a poly(amino acid) or polysaccharide; and
R3=a bond or

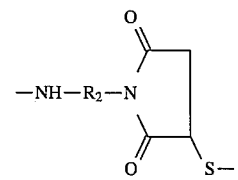

wherein R2=an alkyl, cycloalkyl or aryl group having 2 to 10 carbon atoms.

The derivatives include maleimide conjugates of proteins or poly(amino acids), enzymes, enzyme donor polypeptides and labeling substances. Novel activated hapten intermediates useful in the preparation of the conjugates and methods for synthesis of the hapten intermediates and derivatives are also disclosed.

13 Claims, 5 Drawing Sheets

PIPERIDINE ANALOGS AND CONJUGATES OF PROCAINAMIDE AND NAPA

BACKGROUND

The present invention relates to novel derivatives of procainamide and N-acetylprocainamide (NAPA). The derivatives include immunogens used to stimulate antibody production and polypeptide conjugates useful in immunoassays for detecting procainamide and NAPA. Also provided are hapten intermediates in the synthesis of the immunogens and polypeptide conjugates.

The cardiac depressant drugs procainamide and N-acetylprocainamide are used clinically to treat or prevent cardiac arrhythmia. N-acetylprocainamide (abbreviated as NAPA and also known as acecainide) is the major metabolite of procainamide in man. The concentration of this metabolite in the plasma of patients receiving procainamide often exceeds the concentration of the parent drug itself. Metabolism is by in vivo acetylation, and much genetic-based variation has been observed in the rate at which individual patients transform the drug to its metabolite. This phenomenon is of importance in the clinical use of the drugs because of the lower incidence of side effects associated with NAPA. Both the therapeutic usefulness and the toxicity of the drugs are better correlated with their blood levels than with their dosages. The relationship between the amount of drug administered and the blood levels is quite variable. It is influenced by completeness of absorption, distribution characteristics and rates of metabolism and excretion.

Because of these considerations, numerous analytical methods have been developed to determine blood levels of these drugs, including high pressure liquid chromatography (HPLC), quantitative thin layer chromatography (TLC), and immunoassay, including enzyme immunoassay and immunoassay using fluorescence techniques. Competitive binding immunoassays have proved to be particularly advantageous. In such assays, an analyte in a biological sample competes with a labeled reagent, or analyte analog, or tracer, for a limited number of receptor binding sites on antibodies specific for the analyte and analyte analog. Enzymes, fluorescent molecules, and radioactive compounds are common labeling substances used as tracers. The concentration of analyte in the sample determines the amount of analyte analog which binds to the antibody. The amount of analyte analog that will bind is inversely proportional to the concentration of analyte in the sample, because the analyte and the analyte analog each bind to the antibody in proportion to their respective concentrations. The amount of free or bound analyte analog can then be determined by methods appropriate to the particular label being used.

One type of competitive binding immunoassay is based upon the reassociation of polypeptide fragments to form active enzymes as a step of generating a detectable signal utilized to determine the amount of analyte present in a sample. This type of assay, known as cloned enzyme donor immunoassay (CEDIA), is described in U.S. Pat. No. 4,708,929, the content of which is herein incorporated by reference. In particular, a β-galactosidase enzyme donor polypeptide combines with a β-galactosidase enzyme acceptor polypeptide to form active β-galactosidase enzyme. Conjugating a hapten, or a small analyte or an analyte analogue, to the enzyme donor polypeptide at certain sites does not affect the ability to form β-galactosidase by a complementation reaction and hence does not affect the rate of β-galactosidase activity when in the presence of a substrate for β-galactosidase. However, when the enzyme donor-hapten conjugate is bound by anti-analyte antibody, the complementation rate is impeded, and thereby the enzyme-catalyzed reaction rate during the initial phase of the reaction is reduced. This reduction in enzyme-catalyzed reaction rate can be monitored and has been used to quantitate the determination of a plurality of analytes on the principle of competitive inhibition where enzyme donor-analyte conjugate present in a reaction mixture and analyte present in the sample compete for anti-analyte antibody prior to the addition of enzyme acceptor. The complementation rate of β-galactosidase formation, and hence enzyme catalyzed reaction rate, is increased as the amount of analyte present in the sample is increased.

In accepted clinical practice, procainamide and NAPA are analyzed separately. Therefore immunoassays for NAPA and procainamide require antibodies with a high degree of specificity for either the metabolite or the drug. Since the metabolite and drug differ only by the presence or absence of an acetyl function, the generation of specific antibodies is a particularly challenging problem. Surprisingly, however, the immunogens of the present invention have been found to be especially useful for this purpose.

The preparation of antibodies to procainamide and NAPA for use in immunoassays to determine the drugs has been accomplished in the prior art by essentially three different approaches. One approach has been to couple procainamide through the benzene ring amino group by diazotization and subsequent condensation to an albumin carrier [A. S. Russel et al., *Clin. Exp. Immunol.* 3:901 (1968) and Mojaverian et al., *J. Pharm. Sci.* 69:721 (1980)]. The resulting antibodies show a high degree of cross-reactivity with NAPA, however, and are therefore unsuitable for use in immunoassays specific for one or the other drug.

The second approach involves coupling of the drugs at the opposite end of their structures, at the N-diethylamino group, by modification of one of the ethyl substituents for subsequent coupling to an antigenic carrier. As a result, antibodies are raised against an immunogen in which a major functional group of the drugs has been modified in order to couple them to the carrier. An example of this approach is described in U.S. Pat. No. 4,235,969 issued to Singh et al., in which one of the N-alkyl groups is replaced with a nonoxocarbonyl-alkyl substituent. The nonoxocarbonyl functionality, a linking group containing a carbonyl or imino function, is employed for conjugation to antigens and enzymes. Similarly, European Appl. No. 86103161.5 (Heiman et al.) discloses antigenic conjugates and enzyme conjugates of procainamide analogs modified at the terminal diethylamino group. A specific linking group is attached to a poly(amino acid) or a fluorescein tracer.

In a third approach, Buckler et al., U.S. Pat. No. 4,673,763, describe derivatives of procainamide or NAPA coupled at the α-position of the amide side chain to an immunogenic carrier material or to a label.

The present invention differs from the prior art in the substitution of a non-cyclic diethylamino group with a cyclic piperidine carboxylic acid group. Conjugation to antigens and enzymes is then accomplished through the carboxyl group, either directly or with crosslinkers. In the conjugates of the present invention, piperidine carboxylic acid modified haptens are preferably reacted with aminoalkyl-maleimide crosslinkers to give maleimide adducts of piperidine carboxylic acid haptens. The latter derivatives are reacted with sulfhydryl groups on carrier proteins, enzymes or enzyme donor polypeptides to give thioether linked hapten conjugates. Maleimide/sulfhydryl chemistry [M. Brinkley, *Bioconjugate Chem.* 3:5 (1992)] is more easily controlled than amide bond condensation, thus allowing the preparation of immunogens and enzyme or enzyme donor conjugates with defined, targeted degrees of substitution, a feature which is very important to the functional efficacy of the conjugates. Another example of maleimide derivatives and conjugates of procainamide and NAPA are those described in copending U.S. Ser. No. 08/169,851, filed Dec. 17, 1993, the content of which is incorporated herein by reference.

SUMMARY OF THE INVENTION

The present invention provides novel hapten derivatives of the formula:

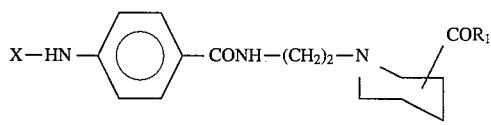

wherein:
X=hydrogen or acetyl, and
$R_1$=hydroxyl or

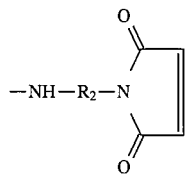

wherein $R_2$=an alkyl, cycloalkyl or aryl group having 2 to 10 carbon atoms, preferably $(CH_2)_2$.

The present invention further provides novel hapten conjugates of the formula:

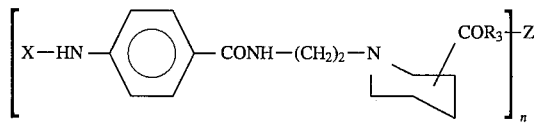

wherein:
X=hydrogen or acetyl;
n=1 to p where p=MW of Z/1000.
Z=an immunogenic poly(amino acid) an enzyme donor polypeptide or a labeling group and
$R_3$=a bond or

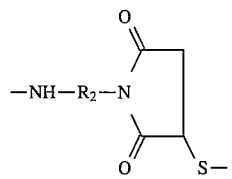

wherein $R_2$=an alkyl, cycloalkyl or aryl group having 2 to 10 carbon atoms, preferably $(CH_2)_2$.

The present invention uniquely provides reagents for use in procainamide and NAPA immunoassays involving the coupling to or derivatization of the maleimide modified activated hapten precursor compound via sulfhydryl groups on a poly(amino acid). The immunogens of the present invention, which comprise the haptenic drug covalently linked via its maleimide moiety and a sulfhydryl bridge to an immunogenic carrier material, are used to stimulate the production of antibodies to the respective drugs.

The present invention further uniquely provides reagents for use in procainamide and NAPA immunoassays involving the coupling to or derivatization of the piperidine carboxylic acid hapten precursor compound via amide linkages to a poly(amino acid). These immunogens of the invention, which comprise the haptenic drug covalently linked via condensation directly with amine groups on an immunogenic carrier material, are used to stimulate the production of antibodies to the respective drugs.

In another aspect, the present invention provides immunoassay methods and reagents for the determination of NAPA and procainamide using the novel antibodies. The present invention also provides novel hapten-enzyme or hapten-enzyme donor conjugates for particularly preferred embodiments of the assay methods. The novel conjugates are prepared from either the activated carboxy piperidine analog or from the maleimide adduct of the piperidine hapten.

BRIEF DESCRIPTION OF THE DRAWINGS

The present invention will be better understood by reference to the following detailed description of the invention when considered in combination with the drawings that form part of the specification, wherein.

DESCRIPTION OF PREFERRED EMBODIMENTS

The present invention, in all of its interrelated embodiments, is focused on the preparation of piperidine carboxylic acid analogs of NAPA and procainamide which can then be used to form immunogens by coupling the derivatives to conventional antigenic poly(amino acid) or other carrier materials and subsequently used to obtain antibodies, or the derivatives can be used to form enzyme, enzyme donor or labeled conjugates which are useful as detection reagents in immunoassays for the drugs.

The chemical structures of NAPA and procainamide are represented by the formula:

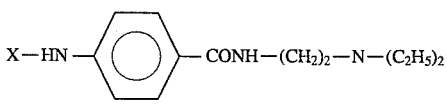

wherein X is hydrogen for procainamide and acetyl for NAPA.

Figure 1:
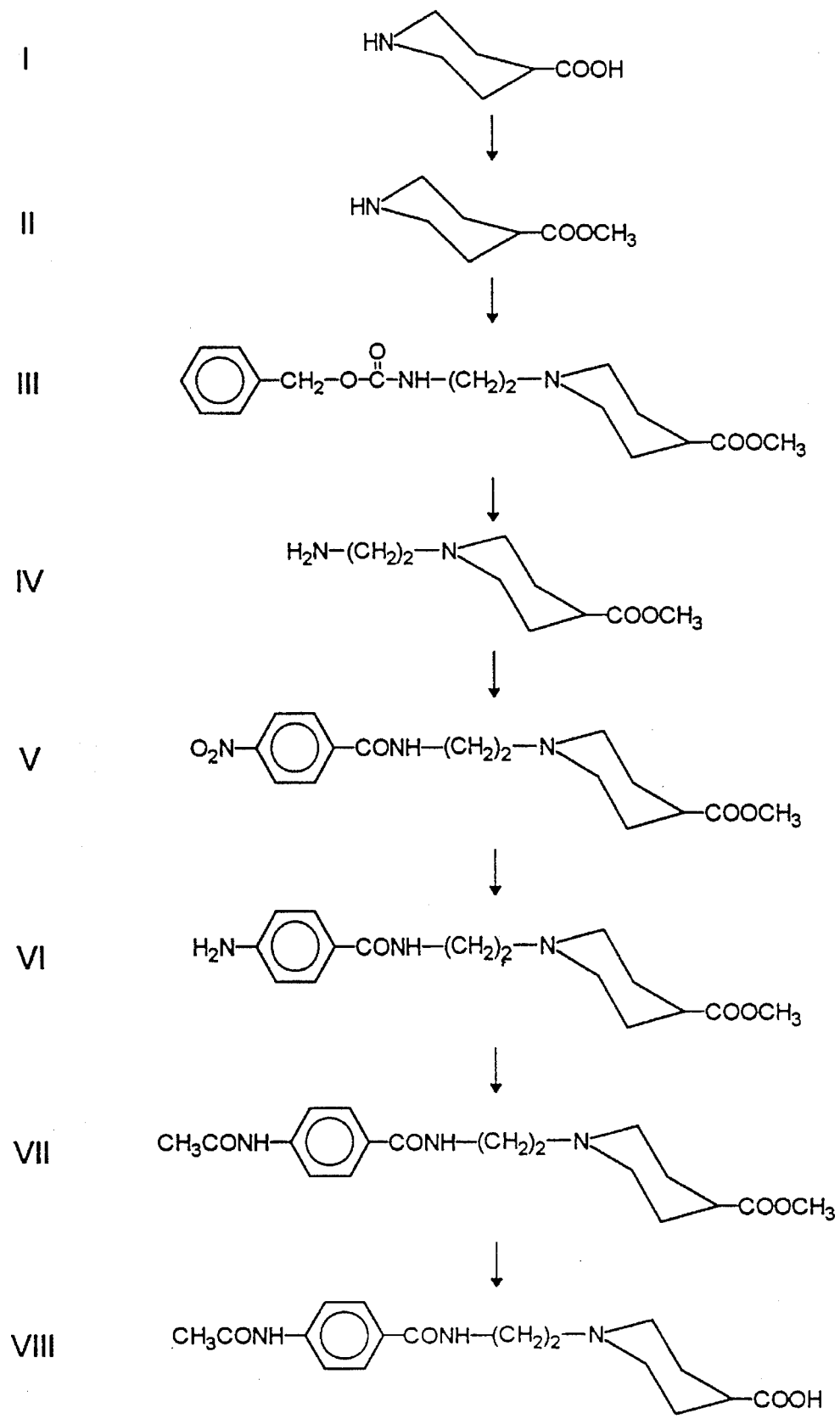
FIG. 1 illustrates a particular synthetic scheme for preparing NAPA piperidine carboxylic acid analog hapten derivatives.

In a preferred embodiment of the present invention, a NAPA piperidine carboxylic acid analog is synthesized according to the scheme given in FIG. 1. 4-Carboxy-piperidine (I) is treated with hydrogen chloride in methanol to give the methyl ester II. Carbobenzoxy-bromoethylamine prepared by the method of E. Katchalski and D. B. Ishai [*J. Org. Chem.* 15:1067 (1950)] is reacted with II in the presence of diisopropylethylamine and potassium carbonate to give the carbobenzoxy-aminoethyl derivative III. Removal of the carbobenzoxy group by catalytic hydrogenation gives the amine IV. The latter intermediate is p-nitrobenzoylated in the presence of diisopropylethylamine and potassium carbonate to give the p-nitrobenzamido-ethyl intermediate V. Hydrogenation of V gives the p-aminobenzamido-ethyl intermediate VI. Acetylation of VI yields the p-acetamidobenzamido-ethyl intermediate VII. Finally, saponification of VII yields the NAPA piperidine carboxylic acid derivative VIII.

Figure 2:
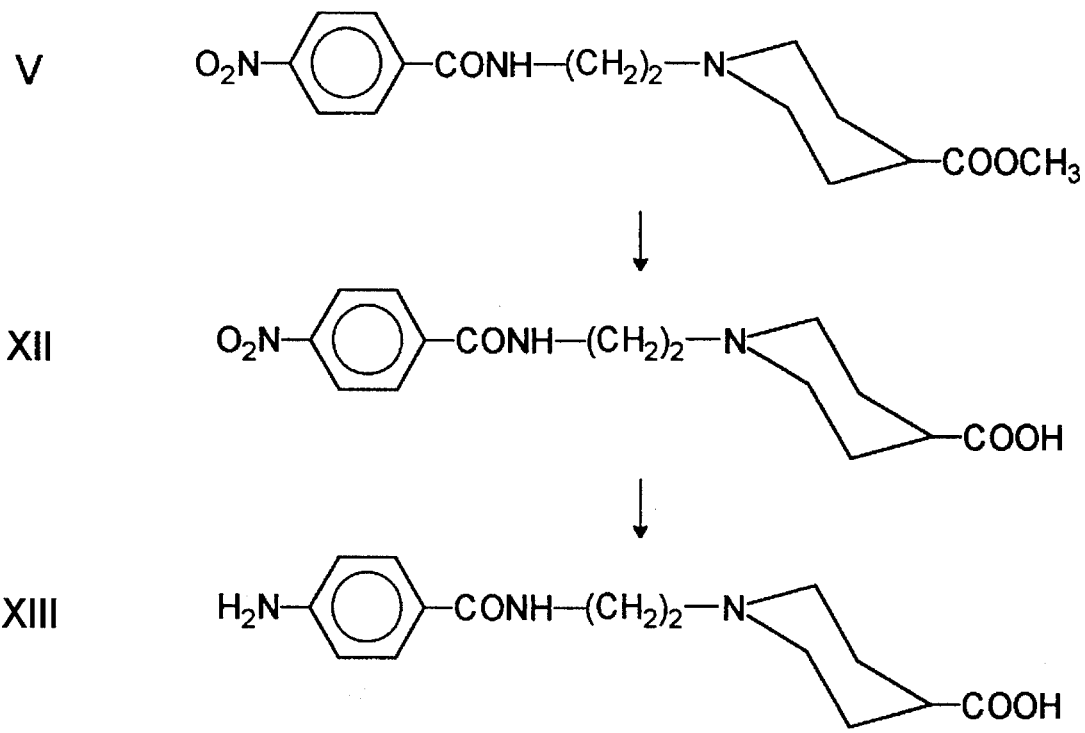
FIG. 2 illustrates a particular synthetic scheme for preparing procainamide piperidine carboxylic acid analog hapten derivatives.

In another preferred embodiment, a procainamide piperidine carboxylic acid analog is synthesized according to the scheme shown in FIG. 2. The p-nitrobenzamido-ethyl intermediate V described above is saponified to give the carboxylic acid XII. Reduction of the nitro group by catalytic hydrogenation yields the procainamide piperidine carboxylic acid analog XIII.

Figure 3:
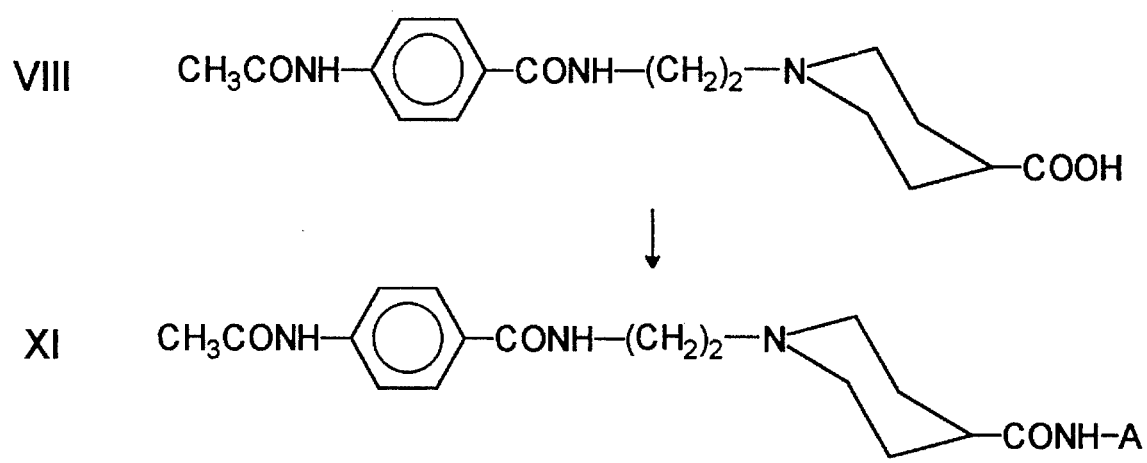
FIG. 3 illustrates particular synthetic scheme for preparing NAPA piperidine carboxylic acid analog conjugates of an antigenic carrier material (A).
Figure 4:
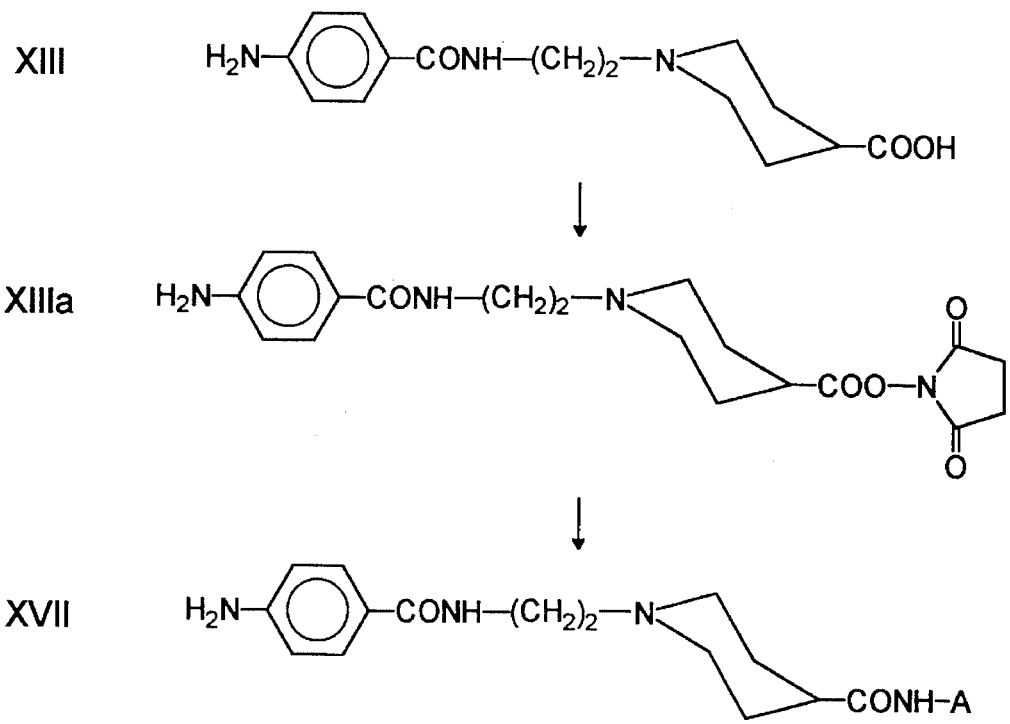
FIG. 4 illustrates a particular synthetic scheme for preparing procainamide piperidine carboxylic acid analog conjugates of an antigenic carrier material (A).

The carboxylic acid analogs may be condensed directly with amine groups on a poly(amino acid) immunogen, enzyme, or enzyme fragment by a condensation reaction in the presence of a carbodiimide to yield amide bond conjugate XI as illustrated in FIG. 3 for the NAPA-piperidine carboxylic acid analog VIII. Alternatively, the carboxylic acid is first converted to an active ester and then condensed in a subsequent reaction with amine groups on the poly(amino acid) to yield the same amide bond conjugate. In the most preferred mode illustrated in FIG. 4 for the procainamide piperidine carboxylic acid analog XIII, the N-hydroxysuccinimide ester XIIIa is first formed by reaction of the carboxylic acid with N,N-disuccinimidyl-carbonate (DSC). The active ester XIIIa is then reacted with poly(amino acid) to yield amide bond conjugate XVII.

Figure 5:
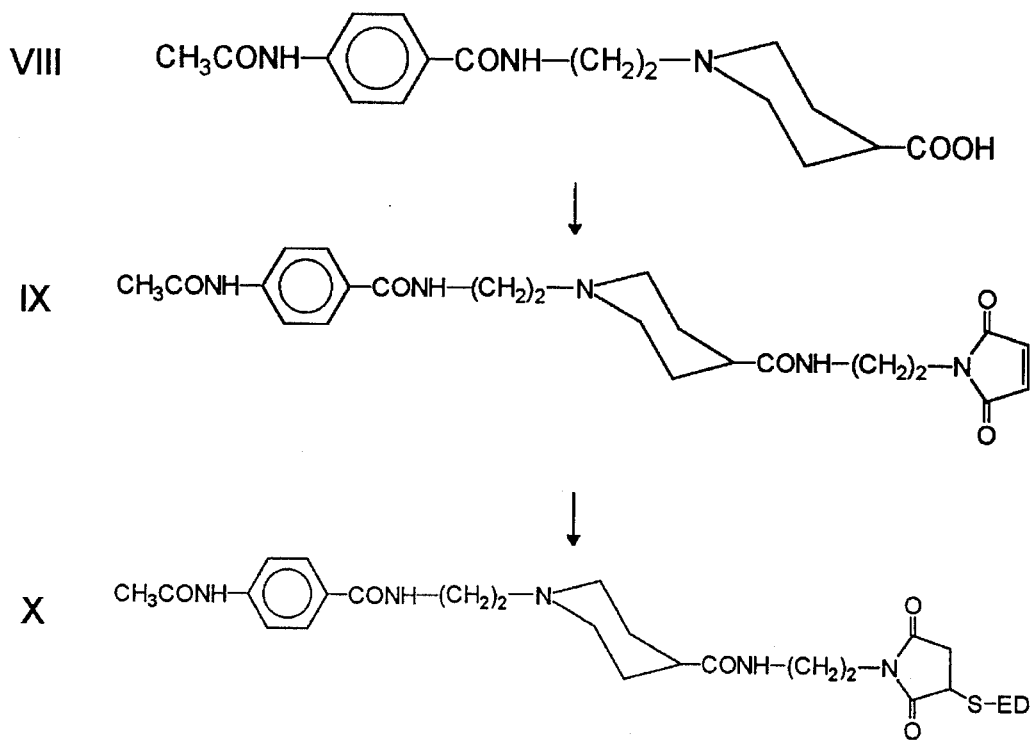
FIG. 5 illustrates a particular synthetic scheme for preparing NAPA piperidine carboxylic acid analog conjugates of an enzyme donor fragment of β-galactosidase (ED).

In yet another preferred embodiment of the invention, in preparing immunogen, enzyme, or enzyme donor conjugates of the analogs, a maleimide adduct is first formed with an aminoalkyl-maleimide derivative. These aminoalkyl-maleimide derivatives are synthesized by the methods of Huber et al. as described in PCT Application No. PCT/EP90/00957, the content of which is incorporated herein by reference. The maleimide adducts are reacted with thiol groups on the immunogen, enzyme or enzyme donor to give thioether-linked conjugate. As illustrated in FIG. 5 for the NAPA piperidine carboxylic acid analog VIII enzyme donor conjugate, condensation with maleimidoethylamine after pre-activation of the carboxylic acid with N-hydroxysuccinimide and a carbodiimide, preferably 1-ethyl-3-(3'-dimethylaminopropyl)-carbodiimide (EDAC), gives the maleimide adduct IX. Reaction of enzyme donor containing cysteine thiol groups with an excess of maleimide adduct gives the conjugate X. The hapten to enzyme donor thiol molar ratio is preferably more than 10 to ensure complete reaction.

Figure 6:
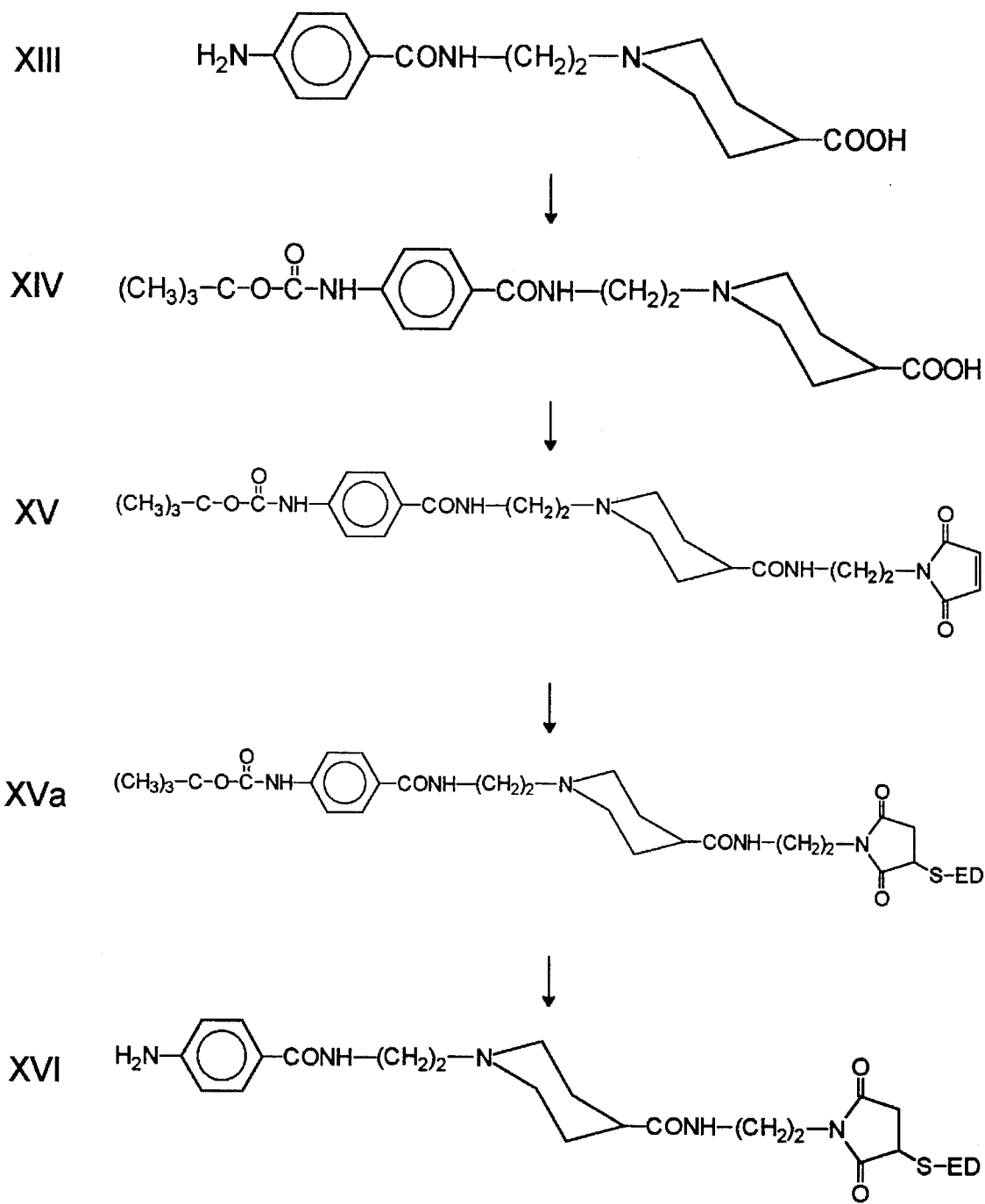
FIG. 6 illustrates a particular synthetic scheme for preparing procainamide piperidine carboxylic acid analog hapten derivatives and conjugates thereof with an enzyme donor fragment of β-galactosidase (ED).

For preparation of a maleimide adduct of the procainamide piperidine carboxylic acid analog XIII as illustrated in FIG. 6, the amino group is first protected as a t-butyloxycarbonyl (BOC) derivative XIV. The BOC intermediate is then condensed with maleimidoethylamine as with the NAPA analog above to give the adduct XV. An excess of the maleimide adduct XV is reacted with enzyme donor thiol groups to give BOC conjugate XVa. Finally, the BOC protection is removed with acid to give the conjugate XVI.

Although the schemes above are illustrated for the NAPA and procainamide piperidine-4-carboxylic acid analogs, it will be obvious to one skilled in the art that the isomeric piperidine 2- and 3-carboxylic acid analogs may be synthesized by the same methods starting with the respective carboxypiperidines.

According to a preferred embodiment, in preparing the immunogens of the invention, a thiol-containing carrier protein or other substance having immunogenic properties is coupled to the maleimide hapten. Although thiolated keyhole limpet hemocyanin (KLH) is an especially preferred antigenic poly(amino acid), or carrier protein, it should be understood that various protein carriers may be employed, including albumins, serum proteins, e.g., globulins, ocular lens proteins, lipoproteins and the like. Illustrative protein carriers include bovine serum albumin, egg ovalbumin, bovine gammaglobulin, thyroxine binding globulin, etc. Alternatively, synthetic poly(amino acids) having a sufficient number of available sulfhydryl groups such as cysteine may be employed, as may other synthetic or natural polymeric materials bearing reactive functional groups. In particular, carbohydrates, yeasts, or polysaccharides may be conjugated to the hapten to produce an immunogen.

Conjugates of the activated hapten and a labelling group such as an enzyme, a substance having fluorescent properties, or a radioactive label may also be prepared and used as reagents in immunoassays. As with the immunogen and enzyme donor conjugates, the label employed must have available thiol-containing groups to be suitable for conjugation via the maleimide linker embodiment of the present invention. The thiol groups may be naturally occurring or they may be artificially introduced using a thiolating agent such as N-succinimidyl-3-(acetylthio) propionate (SATP).

In order to generate antibodies, the immunogen is conveniently prepared for injection into a host animal by rehydrating lyophilized immunogen to form a solution or suspension of the immunogen. The immunogen solution is then combined with an adjuvant such as Freund's. The immunogen may be administered in a variety of sites, at several doses, one or more times, over many weeks.

Preparation of polyclonal antibodies using the immunogen may follow any of the conventional techniques known to those skilled in the art. Commonly, a host animal such as a rabbit, goat, mouse, guinea pig, or horse is injected with the immunogen mixture. Further injections are made, with serum being assessed for antibody titer until it is determined that optimal titer has been reached. The host animal is then bled to yield a suitable volume of specific antiserum. Where desirable, purification steps may be taken to remove undesired material such as nonspecific antibodies before the antiserum is considered suitable for use in performing assays.

Monoclonal antibodies may be obtained by hybridizing mouse lymphocytes, immunized as described above, and myeloma cells using a polyethylene glycol method such as the technique described in *Methods in Enzymology*, vol. 73 (Part B), pages 3–46 (1981).

EXAMPLE 1

Synthesis of N-1-(2-aminoethyl)-4-carboxy-piperidine, p-acetamido-benzamide (VIII)

Piperidine-4-carboxylic acid (I), 12.9 g, was suspended in 200 ml of methanol, and hydrogen chloride gas was bubbled into the suspension while chilling in an ice bath. After 30 min., the resultant solution was warmed up to room temperature and allowed to stand for 24 hr. Rotary evaporation of the solution followed by crystallization of the residue from methanol/diethyl ether gave 14.8 g of methyl 4-carboxy-piperidine hydrochloride (II).

This intermediate, 3.59 g, was suspended in 68 ml of N,N-dimethylformamide (DMF) and treated with 6.95 ml of diisopropylethylamine (DIEA) to generate free base. N-Carbobenzoxy- 2-bromoethylamine [synthesized by the method of E. Katchalski and D. B. Ishai, *J. Org. Chem.* 15:1067 (1950)], 5.16 g, in 32 ml DMF was added followed by 4.3 g anhydrous potassium carbonate. After stirring 19 hr at room temperature, an additional 0.36 g of II was added along with 0.35 ml DIEA in 10 ml DMF. After 3 hr more at room temperature, the reaction mixture was filtered and rotary evaporated at 45° C. to give a solid residue. The residue was redissolved in 150 ml of chloroform and washed successively with 1M aqueous sodium bicarbonate and saturated aqueous sodium chloride solution. The chloroform solution was dried over anhydrous sodium sulfate, filtered and rotary evaporated to give an oil of crude product containing unreacted carbobenzoxy-2-bromoethylamine. Purification was accomplished by redissolving in chloroform, 150 ml, and extracting three times with 80 ml portions of 0.1N hydrochloric acid. The extracts were combined and the pH was brought to about 10 with 1N sodium hydroxide in the presence of chloroform, 100 ml, to back-extract the free base of product. After separating the phases and washing the aqueous phase with additional chloroform, 2×50 ml, the chloroform extracts were combined, dried over sodium sulfate, filtered and rotary evaporated to give an oil which crystallized upon refrigeration. The crystals were collected and washed with petroleum ether to give 3.11 g of methyl N-1-(N'-carbobenzoxy-2-aminoethyl)-4-carboxypiperidine (III), m.p. 37°–39° C. The latter compound, 3.08 g, was dissolved in a mixture of 19 ml 1N hydrochloric acid and 25 ml of methanol. Palladium on charcoal catalyst (5% Pd), 0.44 g, was added and the mixture was hydrogenated at 48 psi in a Parr reactor for 2.5 hr. The suspension was filtered through a bed of celite and the filtrate was rotary evaporated to give an oil. The oil was dried by reevaporation from absolute ethanol, then crystallized from methanol/diethyl ether to give 2.30 g of methyl N-1(2-aminoethyl)-4-carboxypiperidine-dihydrochloride (IV). The amine salt, 1.65 g, was suspended in 33 ml of DMF and DIEA, 1.75 ml, was added to generate the free base. Anhydrous potassium carbonate, 1.40 g, was then added with stirring followed by dropwise addition of a solution of 1.05 g p-nitrobenzoyl chloride in 10 ml DMF. After 1.5 hr at room temperature, the reaction mixture was filtered and rotary evaporated at 40° C. to give an oil. The oil was redissolved in 80 ml chloroform and the solution was washed successively with 3×20 ml portions of 1M sodium bicarbonate followed by saturated sodium chloride solution. The chloroform solution was dried over sodium sulfate, filtered and rotary evaporated to give a semisolid residue which crystallized upon trituration with petroleum ether. The crystals were collected and dried to give 1.45 g of methyl N-1(2-aminoethyl)-4-carboxypiperidine p-nitrobenzamide (V), m.p. 134°–7° C.

The p-nitrobenzamide, 1.25 g, was dissolved in 75 ml methanol and 0.43 g of 5% palladium on charcoal catalyst was added. The mixture was hydrogenated in Parr reactor at 50 psi for 45 min. The catalyst was filtered off using a bed of celite and the filtrate was rotary evaporated to give an oil. Trituration of the oil with diethyl ether gave 1.01 g of crystalline methyl N-1(2-aminoethyl)- 4-carboxy-piperidine-p-aminobenzamide (VI), m.p. 118°–21° C. The latter intermediate, 0.85 g, was dissolved in 20 ml of DMF containing 0.5 ml DIEA. Acetyl chloride, 0.3 ml, was added and the mixture was stirred for 10 min at room temperature. Rotary evaporation gave an oil which was redissolved in 60 ml chloroform, washed with 1M sodium bicarbonate, then dried over anhydrous sodium sulfate. Following filtration and concentration by rotary evaporation to a volume of 10 ml, petroleum ether was added until crystallization ensued. This initial product was recrystallized twice from chloroform/petroleum ether to obtain 0.43 g of purified methyl N-1(2-aminoethyl)-4-carboxy-piperidine p-acetamido benzamide (VII), m.p. 186°–8° C. Finally, 400 mg of the latter material was dissolved in 10 ml methanol and treated with 1N sodium hydroxide, 2.3 ml, for 5.5 hr at room temperature. Rotary evaporation gave an aqueous concentrate which was neutralized to pH 7 with 1N hydrochloric acid and rotary evaporated to dryness. The residue was dried by reevaporating from absolute ethanol. Treatment of the residue with fresh ethanol gave a suspension of sodium chloride which was filtered. Evaporation of the filtrate gave crude product. Crystallization from ethanol gave 0.252 g of N-1(2-aminoethyl)- 4-carboxy-piperidine p-acetamidobenzamide (VIII), m.p. 230°–50° C. (dec). The product gave a single UV absorbing spot by silica gel TLC in the system ethyl acetate/pyridine/acetic acid/water (5:5:1:3). 1H-NMR in DMSO-D6 confirmed the target structure (i.e., multiplets at 1.5, 1.8, 2.0, 2.2, and 2.8 ppm for piperidine CHs; 2.1 ppm singlet for acetyl $CH_3$; 2.4 ppm triplet for $CH_2$—N<pip; 3.3 ppm quartet for CONH—$CH_2$; 7.6 and 7.8 ppm doublets for phenyl ring CHs; 8.3 ppm triplet for benzamide NH; 10.3 ppm singlet for acetamide NH).

EXAMPLE 2

Synthesis of N-1(2-aminoethyl)-4-carboxy-piperidine, p-aminobenzamide (XIII)

Methyl N-1(2-aminoethyl)-4-carboxy-piperidine p-nitrobenzamide (V) synthesized as in described Example 1 above, 1.57 g, was dissolved in 50 ml methanol by warming to about 50° C. The solution was cooled to room temperature and treated with 5 ml of aqueous 1N sodium hydroxide for 1 hr at room temperature. An additional 5 ml of 1N sodium hydroxide was then added and the reaction was continued for 2 hrs at room temperature. After 3 hr, the solution was rotary evaporated to remove about one-third of the methanol and the solution was allowed to stand 3 more hrs at room temperature, then overnight in a refrigerator at 4°–6° C. The reaction solution was then rotary evaporated to remove the remainder of the methanol and the resultant aqueous suspension was diluted with 10 ml water to obtain a solution. The solution was acidified with 1N hydrochloric acid, 10 ml, to give a precipitate of product. The product was collected on a filter and washed with 20 ml each of cold water, diethyl ether, and acetone. Drying gave 1.49 g of N-1(2-aminoethyl)-4-carboxy-piperidine p-nitrobenzamide (XII). The latter intermediate, 1.4 g, was dissolved in a mixture of 30 ml methanol and 4.4 ml of 1N hydrochloric acid. Palladium on charcoal catalyst (5% Pd), 419 mg, was added and the solution was hydrogenated at 50 psi on a Parr reactor for 1.75 hr. The catalyst suspension was filtered through a bed of celite and the filtrate was rotary evaporated to an oil. The oily residue was dissolved in 20 ml water and the pH was adjusted to 6.4 with 1N sodium hydroxide. The solution was rotary evaporated to dryness. The residue was suspended in 20 ml ethanol and reevaporated to remove residual water. The residue was treated with 20 ml of fresh ethanol and the suspension was heated to about 50° C. The suspension was filtered to remove insoluble salt. The filtrate was refrigerated at 4°–6° C. overnight to obtain crystals of product. The crystals were collected and dried to give 0.95 g of N-1(2-aminoethyl)- 4-carboxy-piperidine p-aminobenzamide (XIII). m.p. 148°–58° C. (dec). The product gave a single UV absorbing spot by silica gel TLC in the system ethyl acetate/pyridine/acetic acid/water (5:5:1:3). 1H-NMR in DMSO-D6 confirmed the target structure (i.e., multiplets at 1.55, 1.75, 2.1, 2.2, and 2.85 ppm for piperidine CHs; triplet at 2.45 ppm for $CH_2$-N<pip; multiplet at 3.35 ppm for CONH-$CH_2$; broad singlet at 5.6 ppm for $NH_2$; doublets at 6.55 and 7.55 ppm for phenyl CHs; triplet at 7.95 ppm for CONH).

EXAMPLE 3

Synthesis of
N-1(2-aminoethyl)-4-carboxy-piperidine,
p-(N-t-butyloxycarbonyl)-aminobenzamide) (XIV)

Compound XIII from Example 2, 291 mg, was dissolved in 1.1 ml 1N sodium hydroxide plus 1 ml water. The solution was diluted with 1 ml dioxane. Di-t-butyldicarbonate, 242 mg, was separately dissolved in 1 ml dioxane and added to the solution of XIII with stirring. After 5.5 hr, an additional 102 mg of di-t-butyldicarbonate in 0.8 ml dioxane was added to the reaction. After 3 days, a third portion of 122 mg di-t-butyldicarbonate in 0.5 ml dioxane was added to the reaction and stirring was continued at room temperature for 1 day. The reaction mixture was then neutralized to pH 6 by addition of 1.1 ml of 1N hydrochloric acid. A small amount of product precipitated out and was filtered to give 29 mg. The filtrate solution was passed through a column of Bio-Beads SM-2 resin (Bio-Rad), 1.5×7 cm. The column was washed with 40 ml water, then eluted with 50 ml of 10% acetonitrile/water (v/v) followed by 40 ml of 20% acetonitrile/water (v/v), collecting 10 ml fractions. The product was located by silica gel TLC of fractions in the system 1-butanol/acetic acid/water (3:1:1) with visualization by UV, ninhydin reagent and iodine stain. Fractions containing only product were pooled and rotary evaporated to give a solid residue. The solid was washed with diethyl ether and dried to give 98 mg of product XIV, m.p. 200°–5° C. 1H-NMR showed the presence of a characteristic singlet at 1.5 ppm for t-butyl $CH_3$s.

EXAMPLE 4

Synthesis of N-1(2-aminoethyl)-4-(2-maleimidoethylamidocarbonyl)-piperidine,
p-[(N-t-butyloxycarbonyl)-amino]-benzamide (XV)

Maleimidoethylamine hydrochloride (MEA.HCl) was first synthesized by the method of Huber et al. (Ibid.). N-1(2-aminoethyl)-4-carboxy-piperidine, p-[N-t-butyloxycarbonyl)-amino]benzamide, XIV, 3.22 mg, was dissolved in 0.5 ml DMF. N-Hydroxysuccinimide, 3.05 mg, was added followed by 4.68 mg 1-ethyl-3-(3'-dimethylaminopropyl)-carbodiimide (EDAC). The resultant solution was allowed to stand at room temperature for 5 hr, then stored in a −70° C. freezer for three days. The reaction mixture containing N-hydroxysuccinimide active ester was warmed up to room temperature and 4.36 mg of MEA.HCl was added in 0.5 ml DMF. Triethylamine, 3.43 µl, was then added and the mixture was stirred at room temperature for 90 min. The maleimidoethyl amide product was isolated by HPLC on a semi-preparative C18 reverse phase column (Vydac) equilibrated with 0.1% trifluoroacetic acid (TFA) in water. The product eluted with a 25–35% gradient of 0.1% TFA in acetonitrile over 20 min. as the major UV absorbing peak in the mixture absorbing at 280 or 260 nm. The product was collected and lyophilized to give a total of 6.65 µmol or 3.4 mg based upon UV extinction at the maximum of 267 nm. Note: The extinction coefficient was determined for the starting material, compound XIV, in 0.1% TFA/water and used for compound XV since the incremental contribution of the new maleimidoethyl group in XV to the extinction at this wavelength is negligible. 1H-NMR of compound XV in DMSO-D6 showed the presence of a new resonance at 7.0 ppm for maleimide.

EXAMPLE 5

Synthesis of N-1(2-aminoethyl)-4-(2-maleimidoethylamidocarbonyl)-piperidine
p-acetamidobenzamide (IX)

Similar to Example 4, N-1(2-aminoethyl-4-carboxypiperidine, p-acetamidobenzamide (VIII), 3.4 mg, was dissolved in 0.5 ml DMF. N-hydroxysuccinimide, 4.18 mg, and EDAC, 6.07 mg, were added and the solution was stirred at room temperature for 7 hr. MEA.HCl, 5.41 mg, in 0.5 ml DMF was added followed by triethylamine, 4.26 µl. The mixture was stirred at room temperature for 1 hr. Purification was accomplished by HPLC as in Example 4 except that the gradient range was changed to 10–20%. A total of 2.1 mg was obtained based upon UV absorbance at 268 nm, using an extinction coefficient determined for the starting material VIII. 1H-NMR in DMSO-D6 showed the presence of maleimide as a singlet at 7.0 ppm.

EXAMPLE 6

Conjugation of N-1(2-aminoethyl)-4-(2-maleimidoethylamidocarbonyl)-piperidine,
p-[(N-t-butyloxycarbonyl)-amino]-benzamide (XV)
to a peptide fragment of β-galactosidase The peptide fragment that was used in this example (ED28) consists of β-galactosidase amino acids 1–46, with cysteines at positions 1 and 46. To remove reducing reagent used in the storage buffer for this compound, 3.6 mg of ED28 was desalted on a NAP5™ desalting column (Pharmacia) into 1 ml 50 mM sodium phosphate/1 mM ethylenediaminetetraacetic acid (EDTA), pH 7.0. One µmole (0.44 mg) of compound XV was dissolved in 200 µl of dimethylformamide (DMF). The desalted ED28 was added dropwise to 1 µmole of compund XV while stirring slowly. This was incubated for 1 hr at room temperature. To prepare the sample for HPLC purification, the conjugate mixture was desalted on a NAP5 column equilibrated with water, 0.1% TFA to remove excess hapten. The conjugate was purified on a C4 semi-preparative HPLC column (Vydac) at 4 ml/min using a 25–40% gradient over 15 minutes with solvent A being water/0.1% TFA and B being acetonitrile/0.1% TFA, and the major peak was collected and evaporated to dryness by centrifuging under vacuum in a Spin Vac for 2 hours. The dried conjugate was redissolved in 100% TFA to remove the BOC protecting group and immediately dialyzed against 500 ml of distilled water so that the final TFA concentration was 0.1%. After dialysis overnight, the material was purified on a C4 semi-preparative HPLC column (Vydac) at 4 ml/min using a 25–40% gradient over 15 minutes with solvent A being water/0.1% TFA and B being acetonitrile/0.1% TFA, and the major peak was collected. In this procedure, two moles of compound XV were coupled to each mole of ED28 through the two thiols on the peptide.

EXAMPLE 7

Conjugation of N-(1(2-aminoethyl)-4-(2-maleimidoethylamidocarbonyl)-piperidine p-acetamidobenzamide (IX) to a peptide fragment of β-galactosidase The peptide fragment that was used in this example (ED28) consists of β-galactosidase amino acids 1–46, with cysteines at positions 1 and 46. To remove reducing reagent used in the storage buffer for this compound, 3.6 mg of ED28 was desalted on a NAP5 desalting column into 1 ml 50 mM sodium phosphate/1 mM ethylenediaminetetraacetic acid (EDTA), pH 7.0. One µmole of compound IX was dissolved in 200 µl of dimethylformamide (DMF). Five hundred micrograms ED28 was added dropwise to 1 µmole of compund IX while stirring slowly. This was incubated for 40 min at room temperature. To prepare the sample for HPLC purification, the conjugate mixture was desalted on a NAP5 column equilibrated with water, 0.1% trifluoroacetic acid (TFA) to remove excess hapten. The conjugate was purified on a C4 semi-preparative HPLC column (Vydac) at 4 ml/min using a 25–40% gradient over 15 minutes with solvent A being water/0.1% TFA and B being acetonitrile/0.1% TFA, and the major peak was collected. In this procedure, two moles of compound IX were coupled to each mole of ED28 through the two thiols on the peptide.

EXAMPLE 8

Conjugation of N-1(2-aminoethyl-4-carboxypiperidine p-aminobenzamide (XIII) to KLH and BSA Activation of compound XIII with N,N'-disuccinimidylcarbonate (DSC)

Fifteen mg of DSC was dissolved in 1 ml of dimethylsulfoxide (DMSO). To activate compound XIII, 105 µl of the DSC solution ($6.18 \times 10^{-3}$ mmoles) was added to 1.5 mg of compound XIII ($5.15 \times 10^{-3}$ mmoles) while stirring, 2 µl of triethylamine (TEA) was added, and the mixture was incubated at room temperature for 1 hour.

Coupling of compound XIII to carrier proteins KLH and BSA

Ten mg of bovine serum albumin (BSA) was dissolved in 1 ml of 150 mM sodium carbonate, pH 8.1. In a separate tube, 10 mg of KLH was dissolved in 1 ml of 150 mM sodium carbonate, pH 8.1, and solubilization was enhanced by mild sonication and stirring at room temperature. A 20 molar excess of the DSC-activated compound XIII was reacted with the carrier proteins; therefore, 61.5 µl of compound XIII was added to the BSA solution, and 40.7 µl of compound XIII was added to the KLH solution. These reaction mixtures were incubated for 16 hours at 4° C. The reaction mixtures were transferred to 12,000 to 14,000 molecular weight cutoff Spectrapore™ (Spectrum) tubing and dialyzed against distilled water, 4 L×2 times. Samples were aliquoted into vials (1 mg/vial), frozen at −70° C., and lyophilized. The lyophilized samples were then stored at −20° C. for later use as immunogens.

EXAMPLE 9

Conjugation of N-1(2-aminoethyl)-4-carboxy-piperidine p-acetamidobenzamide (VIII) to KLH and BSA Activation of compound VIII with N,N'-disuccinimidyl carbonate (DSC)

Two mg of compound VIII was activated using a 1.2 molar excess of DSC to modify the carboxylic acid group. In 1.0 ml of dimethylsulfoxide (DMSO), 1.9 mg of DSC was dissolved. Then 2 mg of compound VIII was added to the stirring DSC solution and mixed until completely dissolved. At this point, 2 µl of triethylamine (TEA) was added and the reaction was incubated at room temperature for 1 hour.

Coupling of compound VIII to carrier proteins KLH and BSA

Ten mg of BSA was dissolved in 1 ml of 150 mM sodium carbonate, pH 8.1. KLH was solubilized by dissolving 10 mg in 1 ml of 150 mM sodium carbonate, pH 8.1 and solubilization was enhanced with mild sonication and stirring at room temperature. A 24-fold molar excess of the DSC-activated compound was reacted with the KLH and BSA; therefore, 379 µl of the reaction mixture above was added to the stirring KLH solution and 536 µl of the reaction mixture was added to the BSA solution and incubated 16 hours at 4° C. The reaction mixture was transferred to 12,000 to 14,000 molecular weight cutoff Spectrapore™ tubing and dialyzed against distilled water, 4 L×3 times. Samples were aliquoted into vials (1 mg/vial), frozen at −70° C., and lyophilized. The lyophilized samples were then stored at −20° C. for later use as immunogens.

EXAMPLE 10

Preparation of antibodies

Immunization of host

Preparation of the immunogen and immunization of the host are accomplished using techniques which will be known to those skilled in the art. The immunogen can be prepared for injection into the host animal by rehydrating lyophilized immunogen in phosphate buffered saline (PBS). The antigen solution is then combined with equal amounts by volume of Freund's adjuvant to form an emulsion. The first immunization can be completed with Freund's complete adjuvant and all subsequent immunizations with Freund's incomplete adjuvant. The immunogen may be administered in a variety of sites, at several doses, one or more times, over many weeks.

Selection of antibody

In this example, supernatants were selected from 96-well culture plates using a CEDIA homogeneous assay. As previously described, the CEDIA assay utilizes two genetically engineered, enzymatically inactive fragments of β-galactosidase. The smaller polypeptide, designated the enzyme donor, can recombine spontaneously with the larger fragment, the enzyme acceptor, to form active β-galactosidase, in a process called complementation. When a specific antibody to the ligand attaches to the enzyme donor conjugate, complementation is inhibited. The addition of free ligand to this system will modulate the inhibition of complementation. This assay principle was used to screen fusion products in a 96-well format.

A primary screening of the fusion products was first performed to evaluate the ability of the antibodies to bind to enzyme donor conjugates prepared in Examples 6 and 7 and inhibit complementation. The number of inhibition-positive clones were then narrowed further by performing a secondary screening assay to determine whether the free drug would modulate or compete with the enzyme donor conjugate for the antibody. The modulation assay also identified specific clones when screened against cross reacting analytes. The clones which modulated with the specific analytes of choice were then grown for further study. The culture supernatant containing the monoclonal antibody was collected and evaluated on the HITACHI 717 autoanalyzer (Boehringer Mannheim Corp., Indianapolis, Ind.) as described in Example 6 below.

EXAMPLE 11

Assays for Procainamide and NAPA

CEDIA assays for procainamide and NAPA were performed using the enzyme donor conjugates prepared in Examples 6 and 7 and the antibodies produced according to Example 10. The following reagents were prepared:

| Donor reagent: | |
| --- | --- |
| Enzyme donor conjugate | 0.5 nM |
| Antibody | 1:10–1:100 |
| CPRG (chlorphenylred-β-D-galactopyranoside) | 1 mg/mL |
| NaCl | 500 mM |
| $K_2HPO_4$ | 30 mM |
| EGTA | 10 mM |
| EDTA, Disodium | 0.6 mM |
| Na Azide | 20 mM |
| TWEEN-20 ® | 0.02% |
| pH | 6.80 |
| Acceptor reagent: | |
| Enzyme acceptor | 220 U/ml |
| Magnesium acetate | 5 mM |
| NaCl | 500 mM |
| $K_2HPO_4$ | 30 mM |
| EGTA | 10 mM |
| L-methionine | 10 mM |
| Na Azide | 20 mM |
| TWEEN-20 | 0.02% |
| pH | 6.80 |

® Registered TM of ICI Americas, Inc. for polyoxyethylene sorbitan

Figure 7:
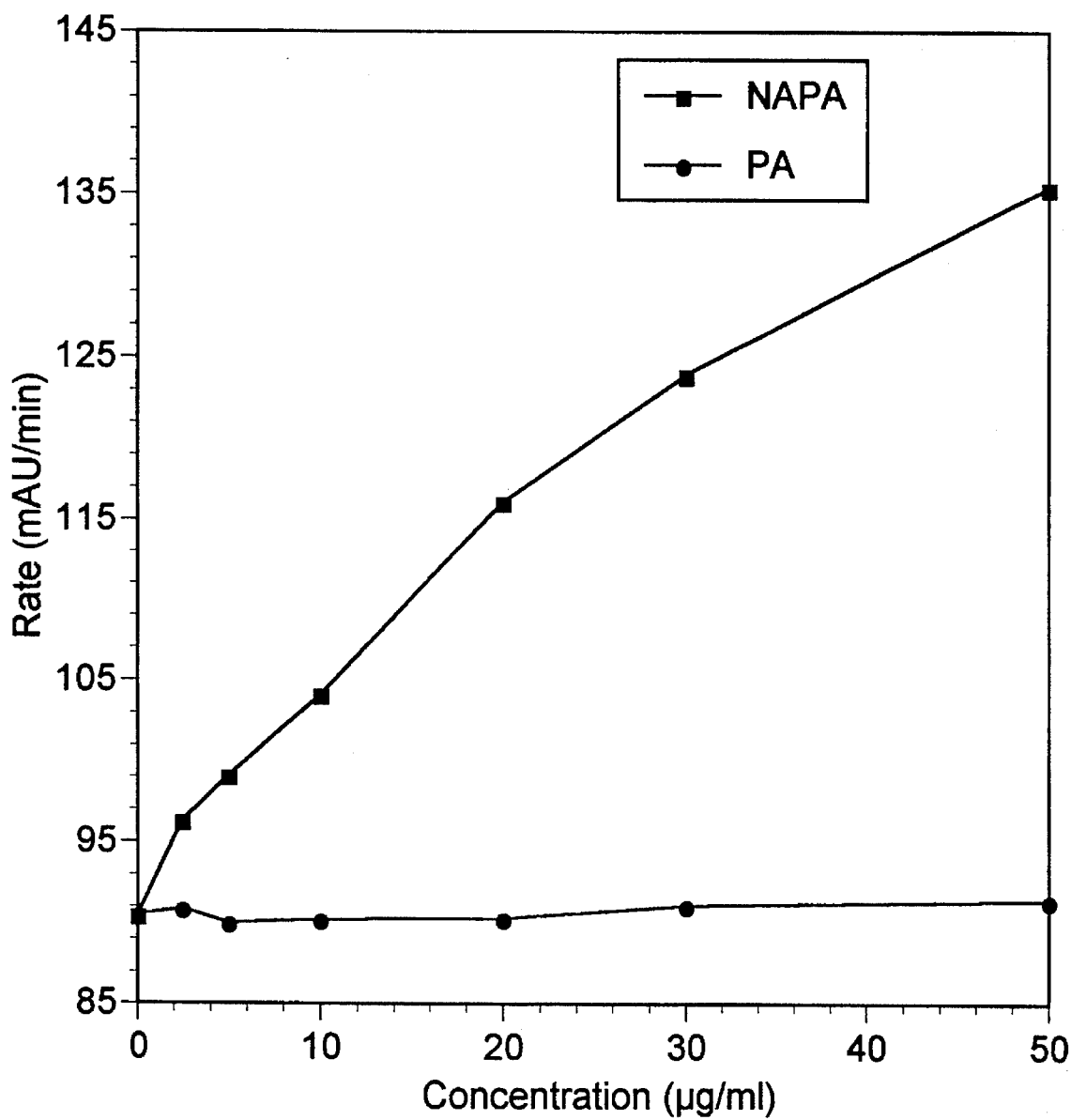
FIG. 7 is a graph showing a dose response curve at varying levels of NAPA using enzyme donor conjugates and antibodies of the present invention in a CEDIA assay.

Assays were performed using an HITACHI 717 autoanalyzer. The instrument dispensed 3 μl of sample containing NAPA or procainamide into a cuvette, and 200 μl of donor reagent was added. The mixture was allowed to incubate at 37° C. for 5 minutes, after which 150 μl of acceptor reagent was added. The absorbance rate was measured over the time period of 243.4 sec to 302.75 sec following the addition of the acceptor reagent. The primary wavelength used was 570 nm, with 660 nm used as the secondary wavelength. The absorbance rate at 570 nm was plotted against procainamide or NAPA concentration to construct a dose response curve. The curve obtained with a NAPA specific monoclonal antibody raised against the immunogen of Example 9 is shown in FIG. 7.

EXAMPLE 12

Evaluation of Antisera to Procainamide (PA)

In this example, sera from mice immunized with N-(1(2-aminoethyl)-4-carboxypiperidine p-aminobenzamide (XIII) conjugated to BSA and KLH (Example 8) were evaluated using the procedures described in Example 11. The following results were obtained:

| | | | Modulation* | |
| --- | --- | --- | --- | --- |
| Antigen | Dilution | (%)Inhibition | NAPA | PA |
| BSA conjugate | 1:400 | 50 | 1 | 30 |
| KLH conjugate | 1:400 | 66 | 5 | 60 |

*At 50 μg/ml

It will be understood that the specification and examples are illustrative but not limitative of the present invention, and that other embodiments within the spirit and scope of the invention will suggest themselves to those skilled in the art.

What is claimed is:

1. A compound of the formula:

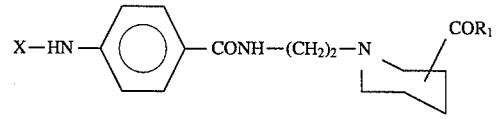

wherein:

X=hydrogen or acetyl, and $R_1$=hydroxyl or

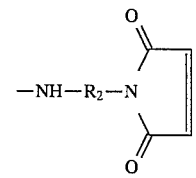

wherein R2=an alkyl, cycloalkyl or aryl group having 2 to 10 carbon atoms.

2. A compound of the formula:

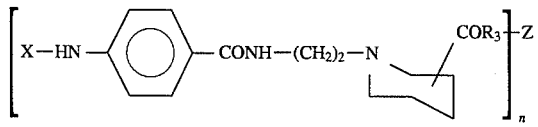

wherein:

X=hydrogen or acetyl;

n=1 to p where p=MW of Z/1000;

Z=an immunogenic poly(amino acid) an enzyme donor polypeptide or a labeling group and R3=a bond or

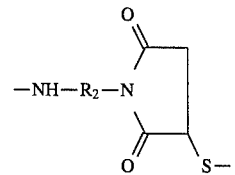

wherein R2=an alkyl, cycloalkyl or aryl group having 2 to 10 carbon atoms.

3. The compound of claim 2, wherein Z is an immunogenic poly(amino acid).

4. The compound of claim 2, wherein Z is an enzyme donor polypeptide.

5. The compound of claim 2, wherein Z is keyhole limpet hemocyanin.

6. The compound of claim 2, wherein Z is an enzyme donor polypeptide of β-galactosidase.

7. The compound of claim 1, wherein $R_2$ is an alkyl group having 2 carbon atoms.

8. The compound of claim 2, wherein $R_2$ is $(CH_2)_2$.

9. A method for determining procainamide in a sample comprising:
   (a) contacting said sample with
      (i) an enzyme donor polypeptide conjugate according to the compound of claim 2, wherein X is hydrogen and Z is an enzyme donor polypeptide of β-galactosidase;
      (ii) an enzyme acceptor polypeptide wherein said enzyme acceptor polypeptide is characterized by forming with said enzyme donor polypeptide conjugate an active enzyme complex having β-galactosidase activity in the absence of an antibody to procainamide;
      (iii) an antibody specific for procainamide, wherein said enzyme donor conjugate is capable of competitively binding to said antibody, thereby inhibiting the formation of active enzyme complex; and
      (iv) a substrate capable of reacting with said active enzyme complex, such that the rate of conversion of said substrate by said active enzyme complex can be monitored, and
   (b) measuring the rate of conversion of said substrate by said active enzyme complex as a measure of the amount of procainamide in said sample.

10. A method according to claim 9, wherein said antibody to procainamide is prepared in immunological response to a compound of the formula:

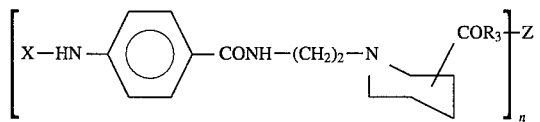

wherein:
   X=hydrogen or acetyl;
   n=1 to p where p=MW of Z/1000;
   Z=an antigenic poly(amino acid); and
   R3=a bond or

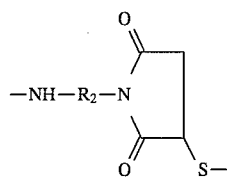

wherein R2=an alkyl, cycloalkyl or aryl group having 2 to 10 carbon atoms.

11. A method for determining NAPA in a sample comprising:
   (a) contacting said sample with
      (i) an enzyme donor polypeptide conjugate according to the compound of claim 2, wherein X is acetyl and Z is an enzyme donor polypeptide of β-galactosidase;
      (ii) an enzyme acceptor polypeptide wherein said enzyme acceptor polypeptide is characterized by forming with said enzyme donor polypeptide conjugate an active enzyme complex having β-galactosidase activity in the absence of an antibody to NAPA;
      (iii) an antibody specific for NAPA, wherein said enzyme donor conjugate is capable of competitively binding to said antibody, thereby inhibiting the formation of active enzyme complex; and
      (iv) a substrate capable of reacting with said active enzyme complex, such that the rate of conversion of said substrate by said active enzyme complex can be monitored, and
   (b) measuring the rate of conversion of said substrate by said active enzyme complex as a measure of the amount of NAPA in said sample.

12. A method according to claim 11, wherein said antibody to NAPA is prepared in immunological response to a compound of the formula:

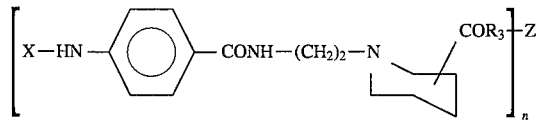

wherein:
   X=hydrogen or acetyl;
   n=1 to p where p=MW of Z/1000;
   Z=an antigenic poly(amino acid); and
   R3=a bond or

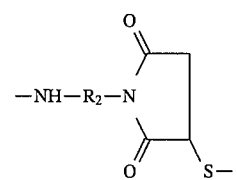

wherein R2=an alkyl, cycloalkyl or aryl group having 2 to 10 carbon atoms.

13. The compound of claim 2, wherein Z is a label selected from the group consisting of an enzyme, a substance having fluorescent properties and a radioactive label.

* * * * *